United States Patent
Park et al.

(10) Patent No.: US 11,859,226 B2
(45) Date of Patent: Jan. 2, 2024

(54) **STRAIN IN *MICROBACTERIUM* AND METHOD FOR PRODUCING PSICOSE USING SAME**

(71) Applicant: SAMYANG CORPORATION, Seoul (KR)

(72) Inventors: Bu-Soo Park, Hanam-si (KR); Eun Jin Han, Seoul (KR); Sang-Hee Lee, Daegu (KR); Soun Gyu Kwon, Gwangmyeong-si (KR); Jin Ha Kim, Hongseong-gun (KR); Chong Jin Park, Daejeon (KR)

(73) Assignee: SAMYANG CORPORATION, Seoul (KR)

(*) Notice: Subject to any disclaimer, the term of this patent is extended or adjusted under 35 U.S.C. 154(b) by 508 days.

(21) Appl. No.: 16/603,213

(22) PCT Filed: Dec. 26, 2017

(86) PCT No.: PCT/KR2017/015477
§ 371 (c)(1),
(2) Date: Oct. 4, 2019

(87) PCT Pub. No.: WO2018/221815
PCT Pub. Date: Dec. 6, 2018

(65) Prior Publication Data
US 2020/0263216 A1 Aug. 20, 2020

(30) Foreign Application Priority Data
Jun. 2, 2017 (KR) .................. 10-2017-0069265

(51) Int. Cl.
*C12P 19/02* (2006.01)
*C12P 1/02* (2006.01)
*C12N 1/20* (2006.01)
*C12R 1/32* (2006.01)

(52) U.S. Cl.
CPC .................. *C12P 1/02* (2013.01); *C12N 1/20* (2013.01); *C12N 1/205* (2021.05); *C12R 2001/32* (2021.05)

(58) Field of Classification Search
CPC ........... C12P 19/02; C12N 1/20; C12N 1/205
See application file for complete search history.

(56) References Cited

FOREIGN PATENT DOCUMENTS

| | | |
|---|---|---|
| AU | 2004236282 | 12/2009 |
| CN | 101177672 | 5/2008 |
| CN | 105849261 | 8/2016 |
| CN | 106164265 | 11/2016 |
| EP | 3388526 | 10/2018 |

(Continued)

OTHER PUBLICATIONS

Corretto,E., Antonielli,L., Sessitsch,A., Kidd,P., Weyens,N. and Brader,G., GenBank entry KJL27122.1, Feb. 13, 2015, accessed at https://www.ncbi.nlm.nih.gov/protein/KJL27122?report=genbank &log$=taxrep&RID=2DPRX96G016 (Year: 2015).*

(Continued)

*Primary Examiner* — David W Berke-Schlessel
*Assistant Examiner* — Trent R Clarke
(74) *Attorney, Agent, or Firm* — LEX IP MEISTER, PLLC (57) ABSTRACT

The present invention relates to a newly isolated bacterium belonging to the genus *Microbacterium*, a composition for producing psicose comprising the strain, and a method for producing psicose using the same.

6 Claims, 3 Drawing Sheets
Specification includes a Sequence Listing.

(56) References Cited

FOREIGN PATENT DOCUMENTS

| | | |
|---|---|---|
| EP | 3564383 | 11/2019 |
| JP | 2017-501729 | 1/2017 |
| JP | 2017-510302 | 4/2017 |
| KR | 10-2006-0125971 | 12/2006 |
| KR | 10-0832339 | 5/2008 |
| KR | 10-2014-0021974 | 2/2014 |
| KR | 10-2014-0122043 | 10/2014 |
| KR | 10-2014-0123284 | 10/2014 |
| KR | 1020140122043 | * 10/2014 |
| KR | 10-1473918 | 12/2014 |
| KR | 10-2016-0081722 | 7/2016 |
| KR | 10-2017-0067070 | 6/2017 |
| WO | 2016-191267 | 12/2016 |

OTHER PUBLICATIONS

Corretto,E., Antonielli,L., Sessitsch,A., Kidd,P., Weyens,N. and Brader,G., GenBank entry KJL31520.1, Feb. 13, 2015, accessed at https://www.ncbi.nlm.nih.gov/protein/KJL31520?report=genbank&log$=taxrep&RID=2FBBPHUZ01R (Year: 2015).*

Midha,S., Bansal,K., Chaudhry,V., Sharma, S., Kumar,N., Patil,P.P. and Patil,P.B., GenBank entry KTR74622.1, Apr. 24, 2015, accessed at https://www.ncbi.nlm.nih.gov/protein/KTR74622?report=genbank&log$=taxrep&RID=2FBBPHUZ01R (Year: 2015).*

EPO, Extended European Search Report of EP 17911921.9 dated Feb. 26, 2021.

Corretto, E., "D-tagatose 3-epimerase [Microbacterium foliorum]", NCBI, Genbank accession No. KJL27133.1 (Mar. 19, 2015).

Deok-Kun Oh et al., "D-Psicose production from D-fructose using an isolated strain, *Sinorhizobium* sp.", Microbiol Biotechnol (2007) 23: 559-563.

Prabla Kumari et al., "*Microbacterium oryzae* sp. nov., an actinobacterium isolated from rice field soil", International Journal of Systematic and Evolutionary Microbiology (2013), 63, 2442-2449.

Longtao Zhang et al., "Characterization of D-tagatose-3-epimerase from Rhodobacter sphaeroides that converts D-fructose into D-psicose", Biotechnol Lett, vol. 31., pp. 857-862 (Feb. 2009).

Hye-Jung Kim et al., "Characterization of an Agrobacterium tumefaciens D-Psicose 3-Epimerase That Converts D-Fructose to D-Psicose", Applied Environmental Microbiology. Feb. 2006; 72(2): 981-985.

KIPO, PCT Search Report & Written Opinion of PCT/KR2017/015477 dated Apr. 9, 2018.

An, MinJi, et al. "90-Day repeated oral toxicity test of D-allulose produced from Microbacterium foliorum." Regulatory Toxicology and Pharmacology 109 (Dec. 2019): 104485. pp. 1-9.

Zhu, Xingxing, et al. "Gene Cloning, Structural Prediction, and Prokaryotic Expression of Agrobacterium tumefaciens D-Psicose-3-Epimerase." Journal of Food Science and Technology 37.3 (May 2019): 61-66.

* cited by examiner

SEQUENCE LISTING

<160> NUMBER OF SEQ ID NOS: 2

<210> SEQ ID NO 1

```
<211> LENGTH: 1409
<212> TYPE: DNA
<213> ORGANISM: Artificial Sequence
<220> FEATURE:
<223> OTHER INFORMATION: Microbacterium oxydans 16S rDNA
<220> FEATURE:
<221> NAME/KEY: misc_feature
<222> LOCATION: (1)..(2)
<223> OTHER INFORMATION: n is A, T, G or C
<220> FEATURE:
<221> NAME/KEY: misc_feature
<222> LOCATION: (4)
<223> OTHER INFORMATION: n is A, T, G or C
<220> FEATURE:
<221> NAME/KEY: misc_feature
<222> LOCATION: (8)
<223> OTHER INFORMATION: n is A, T, G or C
<220> FEATURE:
<221> NAME/KEY: misc_feature
<222> LOCATION: (13)
<223> OTHER INFORMATION: n is A, T, G or C
<220> FEATURE:
<221> NAME/KEY: misc_feature
<222> LOCATION: (915)
<223> OTHER INFORMATION: n is A, T, G or C
<220> FEATURE:
<221> NAME/KEY: misc_feature
<222> LOCATION: (1406)
<223> OTHER INFORMATION: n is A, T, G or C

<400> SEQUENCE: 1
```

| | | | | | |
|---|---|---|---|---|---|
| nngngcgnct | tancatgcag | tcgaacggtg | aagcagagct | tgctctgtgg | atcagtggcg | 60 |
| aacgggtgag | taacacgtga | gcaacctgcc | cctgactctg | ggataagcgc | tggaaacggc | 120 |
| gtctaatact | ggatatgtga | cgtgaccgca | tggtctgcgt | ctggaaagaa | tttcggttgg | 180 |
| ggatgggctc | gcggcctatc | agcttgttgg | tgaggtaatg | gctcaccaag | gcgtcgacgg | 240 |
| gtagccggcc | tgagagggtg | accggccaca | ctgggactga | gacacggccc | agactcctac | 300 |
| gggaggcagc | agtggggaat | attgcacaat | gggcggaagc | ctgatgcagc | aacgccgcgt | 360 |
| gagggatgac | ggccttcggg | ttgtaaacct | cttttagcag | gaagaagcg | aaagtgacgg | 420 |
| tacctgcaga | aaaagcgccg | gctaactacg | tgccagcagc | cgcggtaata | cgtagggcgc | 480 |
| aagcgttatc | cggaattatt | gggcgtaaag | agctcgtagg | cggtttgtcg | cgtctgctgt | 540 |
| gaaatccgga | ggctcaacct | ccggcctgca | gtgggtacgg | gcagactaga | gtgcggtagg | 600 |
| ggagattgga | attcctggtg | tagcggtgga | atgcgcagat | atcaggagga | acaccgatgg | 660 |
| cgaaggcaga | tctctgggcc | gtaactgacg | ctgaggagcg | aaagggtggg | gagcaaacag | 720 |
| gcttagatac | cctggtagtc | cacccgtaa | acgttgggaa | ctagttgtgg | ggtccattcc | 780 |
| acggattccg | tgacgcagct | aacgcattaa | gttccccgcc | tggggagtac | ggccgcaagg | 840 |
| ctaaaactca | aaggaattga | cggggacccg | cacaagcggc | ggagcatgcg | gattaattcg | 900 |
| atgcaacgcg | aagancctta | ccaaggcttg | acatatacga | gaacgggcca | gaaatggtca | 960 |
| actctttgga | cactcgtaaa | caggtggtgc | atggttgtcg | tcagctcgtg | tcgtgagatg | 1020 |
| ttgggttaag | tcccgcaacg | agcgcaaccc | tcgttctatg | ttgccagcac | gtaatggtgg | 1080 |
| gaactcatgg | gatactgccg | gggtcaactc | ggaggaaggt | ggggatgacg | tcaaatcatc | 1140 |
| atgcccctta | tgtcttgggc | ttcacgcatg | ctacaatggc | cggtacaaag | ggctgcaata | 1200 |
| ccgcgaggtg | gagcgaatcc | caaaaagccg | gtcccagttc | ggattgaggt | ctgcaactcg | 1260 |
| acctcatgaa | gtcggagtcg | ctagtaatcg | cagatcagca | acgctgcggt | gaatacgttc | 1320 |
| ccgggtcttg | tacacaccgc | ccgtcaagtc | atgaaagtcg | gtaacacctg | aagccggtgg | 1380 |
| cctaacccct | tgtgaggagcc | tcaagngat | | | | 1409 |

```
<210> SEQ ID NO 2
<211> LENGTH: 1478
<212> TYPE: DNA
<213> ORGANISM: Artificial Sequence
<220> FEATURE:
<223> OTHER INFORMATION: Microbacterium phylloshaerae 16S rDNA

<400> SEQUENCE: 2
gatgaacgct ggcggcgtgc ttaacacatg caagtcgaac ggtgaagccc agcttgctgg      60
gtggatcagt ggcgaacggg tgagtaacac gtgagcaacc tgccctgac tctgggataa     120
gcgctggaaa cggcgtctaa tactggatac gagtagcgac cgcatggtca gttactggaa    180
agatttattg gttggggatg ggctcgcggc ctatcagctt gttggtgagg taatggctca    240
ccaaggcgtc gacgggtagc cggcctgaga gggtgaccgg ccacactggg actgagacac    300
ggcccagact cctacgggag gcagcagtgg ggaatattgc acaatgggcg caagcctgat    360
gcagcaacgc cgcgtgaggg atgacggcct tcgggttgta aacctctttt agcagggaag    420
aagcgaaagt gacggtacct gcagaaaaag cgccggctaa ctacgtgcca gcagccgcgg    480
taatacgtag ggcgcaagcg ttatccggaa ttattgggcg taaagagctc gtaggcggtt    540
tgtcgcgtct gctgtgaaat ccggaggctc aacctccggc ctgcagtggg tacgggcaga    600
ctagagtgcg gtaggggaga ttggaattcc tggtgtagcg gtggaatgcg cagatatcag    660
gaggaacacc gatggcgaag gcagatctct gggccgtaac tgacgctgag gagcgaaagg    720
gtggggagca acaggctta gataccctgg tagtccaccc cgtaaacgtt gggaactagt    780
tgtggggtcc attccacgga ttccgtgacg cagctaacgc attaagttcc ccgcctgggg    840
agtacggccg caaggctaaa actcaaagga attgacgggg acccgcacaa gcggcggagc    900
atgcggatta attcgatgca acgcgaagaa ccttaccaag gcttgacata tacgagaacg    960
ggccagaaat ggtcaactct ttggacactc gtaaacaggt ggtgcatggt tgtcgtcagc   1020
tcgtgtcgtg agatgttggg ttaagtcccg caacgagcgc aaccctcgtt ctatgttgcc   1080
agcacgtaat ggtgggaact catgggatac tgccggggtc aactcggagg aaggtgggga   1140
tgacgtcaaa tcatcatgcc ccttatgtct tgggcttcac gcatgctaca atggccggta   1200
caaagggctg caataccgcg aggtggagcg aatcccaaaa agccggtccc agttcggatt   1260
gaggtctgca actcgacctc atgaagtcgg agtcgctagt aatcgcagat cagcaacgct   1320
gcggtgaata cgttcccggg tcttgtacac accgcccgtc aagtcatgaa agtcggtaac   1380
acctgaagcc ggtggcctaa cccttgtgga gggagccgtc gaaggtggga tcggtaatta   1440
ggactaagtc gtaacaaggt agccgtaccg gaaggtgc                           1478
```

STRAIN IN *MICROBACTERIUM* AND METHOD FOR PRODUCING PSICOSE USING SAME

This application claims the benefit of Korea Patent Application No. 10-2017-0069265 filed on Jun. 2, 2017 with the Korea Industrial Property Office, the entire disclosure of which is hereby incorporated by reference.

TECHNICAL FIELD

The present invention relates to a bacterium belonging to a bacterium of genus *Microbacterium*, a composition for producing psicose comprising the bacterium, and a method for producing psicose using the same.

BACKGROUND ART

Psicose is an epimer of no. 3 carbon of fructose (D-fructose). It has the sweetness degree corresponding to 70% compared to fructose, but it is hardly metabolized at the internal absorption in body unlike the fructose and it has a function to inhibit absorption of glucose and inhibit blood glucose. Therefore, it can be used for food and drink for diabetes patients or food and drink for guarding a body, and it can be used for various foods like health food, etc., because it has a function to inhibit an activity of enzyme involved in lipid synthesis in liver and thus it has a function to control blood sugar, prevent a cavity, and inhibit fat synthesis in liver, such as inhibiting accumulation of abdominal fat.

Sugar alcohols largely used as a sweetener substituted for sugar have side effects like causing diarrhea when absorbed over certain amount, etc., but psicose does not have a known side effect. Therefore, the psicose has been attracted as a diet sweetener, but the development of technology for effectively preparing the psicose is required to apply it into the food industry, as it belongs to a rare sugar which is a monosaccharide present in nature extremely rarely.

The conventional method for preparing the psicose is to prepare it mainly passing through chemical synthesis process like a chemical method of producing the psicose from a fructose using a catalytic action of molybdic acid ion. However, the chemical synthesis has a problem in that the psicose is present in a very small amount in a syrup treatment process or glucose isomerization process and it is costly and it produces a byproduct.

To solve such a problem, a biological method for preparing the psicose by an enzymatic reaction with a fructose as a substrate, such as producing the psicose from the fructose by psicose epimerase derived from *Agrobacterium tumefaciens* has been researched.

However, according to the conventional enzymatic method by using the enzyme with known function, the enzymes producing the psicose exhibit the optimum under the pH of alkaline condition, but the reaction under the alkaline condition induces non-specific reaction and browning of sugar, and therefore, it is not appropriate for industrialization. In addition, the conventional enzymes have a problem in that the yield of psicose production applied for industrialization is low and the manufacturing cost is increased as they have decreased stability or slow reaction rate at the high temperature. Thus, a method for producing a psicose with high yield under temperature condition being suitable for industrialization without producing a byproduct has been required.

DISCLOSURE

Technical Problem

One embodiment of the present invention provides a bacterium of *Microbacterium* genus having a psicose conversion activity to produce a psicose from a fructose.

Another embodiment of the present invention provides a composition for producing a psicose comprising a cell of the *Microbacterium* genus, a culture of the bacterium, a supernatant of culture of the bacterium, an extract of culture of the bacterium, and/or a lysate of the bacterium.

Other embodiment of the present invention provides a method for producing a psicose from a fructose using the bacterium of *Microbacterium* genus.

Other embodiment of the present invention provides a method for isolating a *Microbacterium* genus to produce an enzyme which converts a fructose into psicose.

Technical Solution

The present inventor isolated and identified a novel *Microbacterium* genus (for example, *Microbacterium oxydans* or *Microbacterium phyllosphaerae*) having an excellent activity of converting a fructose to a psicose, and found the conversion activity from the fructose to psicose by using microbial cells of the bacterium, and studied the optimum temperature the optimum reaction time of microbial cell reaction required for obtaining the high conversion activity of psicose, thereby establishing the condition for effective mass production of psicose, to complete the present invention.

One embodiment of the present invention provides a novel bacterium belonging to the genus *Microbacterium* of converting a fructose to psicose. The bacterium belonging to the genus *Microbacterium* may be *Microbacterium oxydans* or *Microbacterium phyllosphaerae*. For examples, the bacterium may be *Microbacterium oxydans* SYG-A1 strain deposited as an accession number KCCM12033P or *Microbacterium phyllosphaerae* SYG-A2 strain deposited as an accession number KCCM12034P The bacterium belonging to the genus *Microbacterium* is characterized by having excellent psicose conversion activity of converting a fructose to a psicose. The psicose conversion activity is obtained as the bacterium belonging to the genus *Microbacterium* produces an enzyme converting a fructose to a psicose, and the *Microbacterium* genus may produce an enzyme having high psicose conversion activity, or may produce the psicose convertase in quantity, to exhibit excellent psicose conversion activity. Thus, the bacterium belonging to the genus *Microbacterium* may be usefully applied for preparation of psicose, and may enhance the yield of psicose production.

The psicose conversion activity may have the activity under the condition of temperature of 30° C. or higher or 40° C. or higher, and for example, may exhibit the maximum activity under the condition of temperature of 40 to 80° C. 50 to 80° C. 60 to 80° C., 65 to 75° C., or 70 to 80° C. for example, 70° C.

In addition, when the substrate of fructose is reacted by using the bacterium belonging to the genus *Microbacterium* in the method for preparing a psicose, the conversion rate of psicose is increased as the reaction time is longer. For example, it is preferable that the reaction time is 1 hour or higher, for example, 2 hours or higher, 3 hours or higher, 4 hours or higher, 5 hours or higher or 6 hours or higher. In addition, since the increasing rate of conversion rate of psicose is insignificant or rather decreased, when the reaction time is over 48 hours, it is preferable that the reaction time does not exceed 48 hours. Therefore, the reaction time may be 1 to 48 hours, 2 to 48 hours, 3 to 48 hours, 4 to 48 hours, 5 to 48 hours, or 6 to 48 hours, and it may be approximately 1 to 48 hours, 2 to 36 hours, 3 to 24 hours, 3 to 12 hours, or 3 to 6 hours, in consideration of industrial and economical aspects, but not limited thereto.

The relative activity (%) of the bacterium belonging to the genus *Microbacterium* may have 9 to 30%, preferably 9 to 25%, or more preferably 9 to 20%, when it reacts with fructose at 70° C. for 18 hours. For example, when *Microbacterium oxydans* reacts with fructose at 70° C. for 18 hours, its relative activity (%) may be 9 to 15%, or preferably 9 to 12%. when *Microbacterium phyllosphaerae* reacts with fructose at 70° C. for 18 hours, its relative activity (%) may be 15% to 30%, preferably 15 to 25%, or more preferably 15 to 20%.

The method for preparing a psicose proposed in the present invention can concert a fructose to a psicose by not using a buffer solution and using a microbial cell, and thus it has an advantage of producing a psicose with high yield by a simpler method.

The description of the bacterium of *Microbacterium* genus having a psicose conversion activity and the composition for producing a psicose comprising the the bacterium of *Microbacterium* genus can be applied to a method for producing a psicose from a fructose using the bacterium of *Microbacterium* genus.

The bacterium of *Microbacterium* genus can be at least one selected from the group consisting of a microbial cell of the *Microbacterium* genus, a culture of the bacterium, and a lysate of the bacterium. The step of reacting the bacterium of *Microbacterium* genus with the fructose can be carried out by reacting the bacterium with a fructose-containing substrate.

In other specific embodiment, the step of reacting the bacterium belonging to the genus *Microbacterium* with fructose-containing substrate may be performed by a step of contacting the bacterium (e.g., microbial cells, culture of bacterium, and/or lysate of bacterium) with a fructose, for example, a step of mixing the bacterium with fructose-containing substrate or a step of contacting fructose-containing substrate with a support in which the bacterium is immobilized. As such, by reacting the bacterium belonging to the genus *Microbacterium* with a fructose, a psicose may be produced from a fructose by converting fructose into psicose.

In the method for preparing a psicose, for effective production of psicose, the concentration of fructose used as a substrate may be 40 to 75% (w/v), 45 to 75% (w/v), for example, 50 to 75% (w/v), based on the total reactants. When the concentration of fructose is lower than the range, the economic becomes lower, and when it is higher than the range, the fructose is not dissolved well, and thus the concentration of fructose in the range is preferable. The fructose may be used as a liquid state dissolved in a buffer solution or water (for example, distilled water).

In the method for preparing a psicose, the reaction may be performed under the condition of temperature of 30° C. or higher, for example, 40° C. or higher. Since the browning of fructose as a substrate may be caused, when the temperature is 80° C. or higher, the reaction may be performed under the condition of 40 to 80° C., for example, 50 to 80° C., 60 to 80° C., or 65 to 75° C., for example, 70° C.

In addition, the reaction may be performed under the condition of pH 6.5 to 9.0, for example, pH 7.0 to 9.0, pH 7.5 to 9.0, pH 8.0 to 9.0 or 8.5 to 9.0, In particular, the effective production of psicose is possible even in the neutral pH range of pH 7.0 to 8.0.

The method for preparing a psicose proposed in the present invention can convert a fructose to a psicose by using a microbial cell but not using a buffer solution and, and thus it has an advantage of producing a psicose with high yield by a simpler method.

In another embodiment of the present invention, it is to provide with a composition for producing a psicose comprising a bacterium belonging to the genus *Microbacterium* having a psicose conversion activity from fructose.

The description of the bacterium belonging to the genus *Microbacterium* having a psicose conversion activity from fructose in the above can be applied to the composition for producing a psicose.

For examples, the bacterium of the genus *Microbacterium* may be a *Microbacterium oxydans* or *Microbacterium phyllosphaerae* strain. For examples, the bacterium may be *Microbacterium oxydans* SYG-A1 strain deposited as an accession number KCCM12033P or *Microbacterium phyllosphaerae* SYG-A2 strain deposited as an accession number KCCM12034P.

The bacterium belonging to the genus *Microbacterium* may include one or more selected from the group consisting of the microbial cell of the *Microbacterium* genus, a culture of the bacterium, and a lysate of the bacterium.

The culture comprises an enzyme produced from the bacterium belonging to the genus *Microbacterium* in and may comprise the bacterium or be a cell-free form of not comprising the bacterium. The lysate means a lysate of crushing the bacterium belonging to the genus *Microbacterium* or a supernatant obtained by centrifuging the lysate, and includes an enzyme produced from the bacterium belonging to the genus *Microbacterium*.

Herein, unless otherwise stated, the bacterium belonging to the genus *Microbacterium* used for preparation of psicose is used for meaning at least one selected from the group consisting of a microbial cell of the bacterium, a culture of the bacterium, and a lysate of the bacterium.

In the composition, the concentration of microbial cells of bacterium belonging to the genus *Microbacterium* may be 1 mg (dcw: dry cell weight)/ml or higher, for example, 1 to 50 mg(dcw)/ml. When the concentration of microbial cells is less than the range, the psicose conversion activity is low or little, and when it exceeds the range, the total efficiency of psicose conversion reaction is lower as microbial cells are too many, and the range of the concentration of microbial cells is preferable.

Since the activation of an enzyme converting a fructose that the strain of *Microbacterium* genus produces into a psicose (for example, epimerase) may be controlled by a metal ion, in the production of psicose using the bacterium belonging to the genus *Microbacterium*, when a metal ion is added, the conversion efficiency from a fructose into a psicose, the production rate of psicose may be increased.

Therefore, the composition for preparing a psicose comprising the bacterium belonging to the genus *Microbacterium* may further comprise a metal ion. In addition, the method for preparing a psicose using the bacterium belonging to the genus *Microbacterium* may further comprise a step of adding a metal ion.

In one embodiment, the metal ion may be added in a culture medium in the culturing step, or the culturing step may be performed in a culture medium in which the metal ion is added. In another embodiment, the metal ion may be added to a fructose or added to the mixture of the bacterium belonging to the genus *Microbacterium* and fructose. In other embodiment, it may be added to a support in which the bacterium belonging to the genus *Microbacterium* is immobilized (before adding a fructose), or added to the mixture of support in which the bacterium belonging to the genus *Microbacterium* is immobilized and fructose (after adding a fructose), or it may be added in a form of mixture with a fructose or respectively as adding a fructose.

The metal ion may be at least one selected from the group consisting of copper ion, manganese ion, calcium ion, magnesium ion, zinc ion, nickel ion, cobalt ion, iron ion, aluminum ion, etc. For example, the metal ion may be at least one selected from the group consisting of manganese ion, magnesium ion, nickel ion, cobalt ion, etc., and in one embodiment, the metal ion may be a manganese ion, a cobalt ion, or the mixture thereof.

The support may create an environment in which the activity of immobilized strain or enzyme produced from the strain can be maintained for a long period, and it may be all supports publicly known to be used for enzyme immobilization.

For example, sodium alginate may be used as the support. The sodium alginate is a polysaccharide abundantly present in a cell wall of seaweed, and is composed of mannuronic acid (β-D-mannuronic acid) and gluronic acid (α-L-gluronic acid), and forms beta-1,4 bond randomly in the aspect of content, and thereby the strain or enzyme is immobilized stably, and thus it is advantageous to exhibit the excellent psicose yield.

In one specific embodiment, for further enhancing the yield of psicose, a solution of sodium alginate of 1.5 to 4.0% (w/v) concentration (for example, sodium alginate aqueous solution), for example, a solution of sodium alginate of approximately 2.5% (w/v) concentration may be used for immobilization of strain. For example, after adding microbial cells of the strain, a culture comprising the enzyme produced by the strain, or a lysate of the strain to the sodium alginate aqueous solution in 1 to 2 volume times of microbial cells of strain, the culture comprising the enzyme produced by the strain or the lysate of the strain and mixing, by producing a bead by dropping the obtained mixed solution to approximately 0.2M calcium ion solution by using a syringe pump and a vacuum pump, the microbial cells of the strain, culture comprising the enzyme produced by the strain, or lysate of the strain may be immobilized in the sodium alginate support. The enzyme may be purified from the strain, strain culture or lysate of strain by methods such as common methods, for example, methods of dialysis, precipitation, adsorption, electrophoresis, affinity chromatography, ion exchange chromatography, etc.

In an embodiment of the present invention, it is to provide with a method for producing a psicose from a fructose using the bacterium of *Microbacterium* genus having a psicose conversion activity to produce a psicose from a fructose.

Effect of the Invention

The present invention relates to a newly isolated bacterium belonging to the genus *Microbacterium*, a composition for producing psicose comprising the strain, and a method for producing psicose using the same, and since the bacterium belonging to the genus *Microbacterium* of the present invention has a stability in a useful range of temperature and has an activity to produce a psicose from a fructose with high yield, it is expected that it would be widely used in functional sugar-related health food and pharmaceutical industries.

DETAILED DESCRIPTION OF THE EMBODIMENTS

The present invention will be described in more detail by the following examples. However, the following examples are desirable examples of the present invention, and the present invention is not limited thereto.

Example 1. Isolation of Microorganism Converting Fructose into Psicose

To isolate a strain converting a fructose into a psicose, 1% (w/v) psicose-added Mineral salt broth ($KH_2PO_4$ 2.4 g/L, $K_2HPO_4$ 5.6 g/L, $(NH_4)_2SO_4$ 2.6 g/L, $MgSO_4 7H_2O$ 0.1 g/L, yeast extract 1 g/L) was used.

Each 1 g sample of soils obtained from orchard or fertile land, cheese, milk, edible flower, broccoli and ginseng was selected, and 1 g of each food was collected and added to MSP broth, and then cultured at 30° C. with agitation for 24 hours, thereby implementing enrichment. Then, 100 µL (microliter) of culture solution was collected and smeared on an agar medium, and then cultured at 30° C. until the colony was confirmed. Colonies having different shapes and sizes among colonies formed in the agar medium were selected and inoculated into MSP broth, and then shaking cultured at 30° C. for 24 hours and centrifuged to recover only microbial cells. The recovered microbial cells were put into 100 µL of 50 mM PIPES (piperazine-N, N'-bis(2-ethanesulfonic acid)) buffer solution (pH 7.0) and suspended, and lysated by using a ultrasonic processor (ColepParmer) to collect a lysate solution. After centrifuging the lysate solution by 12,000 rpm at 4° C. for 10 mM, the supernatant was recovered and used as an enzyme solution (crude enzyme), and the enzyme solution was reacted at 30° C. for 12 hours with 10 mM fructose and psicose as substrates.

Whether the psicose was converted into the fructose in the reaction solution was confirmed by Thin Layer Chromatography (TLC) analysis. The thin layer chromatography analysis was performed by using a developing solvent of a stationary phase of silica gel (Silica gel 60F254 (Merck, Germany)) of width 20 cm, height 10 cm and a mobile phase mixing acetonitrile and water at the volume ratio of 85:15 and developing by 3 times for 10 min.

The strains in which a psicose was converted to a fructose confirmed by the TLC analysis were sorted and inoculated into 0.1% (w/v) psicose-added MS broth and shaking cultured at 30° C. for 24 hours, and after centrifugation, only microbial cells were recovered. The recovered microbial cells were washed with 0.85% (w/v) NaCl, and then suspended by putting 400 g/L fructose and 1 mM manganese ion-added 50 mM PIPES buffer solution (pH 7.0), and reacted at 70° C. for 1 hour.

Then, after recovering the supernatant by centrifuging the reaction results, High-Performance Liquid Chromatography (HPLC) analysis was carried out. The liquid chromatography analysis was performed by using RID (Refractive Index Detector, Agilent 1260 RID) of HPLC (Agilent, USA) equipped with Aminex HPX-87C column (BIO-RAD). Water was used as a mobile phase and the temperature was 80° C., and the flowing rate was 0.6 mL/min. The obtained result was shown in FIG. 1, and two strains which produced psicose the most among several thousand kinds of strains was finally selected.

Example 2. Identification of Strain Having Psicose Conversion Activity

The sequence of 16S ribosome RNA was confirmed to identify the strain isolated in Example 1. It was confirmed that the sequences (5'→3') of 16S ribosome RNA of isolated strains were shown in SEQ ID NO: 1 or SEQ ID NO: 2, respectively.

The strain with 16S rRNA shown in SEQ ID NO:1 was 78.76% of nucleotide sequence identity to *Microbacterium oxidans* DSM20578, and it was named *Microbacterium oxidans* SYG-A1. The strain was deposited to Korean Culture Center of Microorganisms (Address: Yurim Building, 45, Hongjenae 2ga-gil, Seodaemun-gu, Seoul, Korea), an international depository authority, on May 26, 2017 under the provisions of the Budapest Treaty and the accession number KCCM12033P was given.

The strain with 16S rRNA shown in SEQ ID NO:2 was 100% of nucleotide sequence identity to *Microbacterium phyllosphaerae* P369/016(NP_025405.1), and it was named *Microbacterium phyllosphaerae* SYG-A2. The strain was deposited to Korean Culture Center of Microorganisms (Address: Yurim Building, 45, Hongjenae 2ga-gil, Seodaemun-gu, Seoul, Korea), an international depository authority, on May 26, 2017 under the provisions of the Budapest Treaty and the accession number KCCM12034P was given.

Example 3. Establishment of Optimum Temperature Condition Using Microbial Cell Reaction of the Strains For the isolated strains, microbial cells and a substrate were reacted under various conditions of temperature and metal ion, and the psicose conversion activities were compared.

Figure 2:
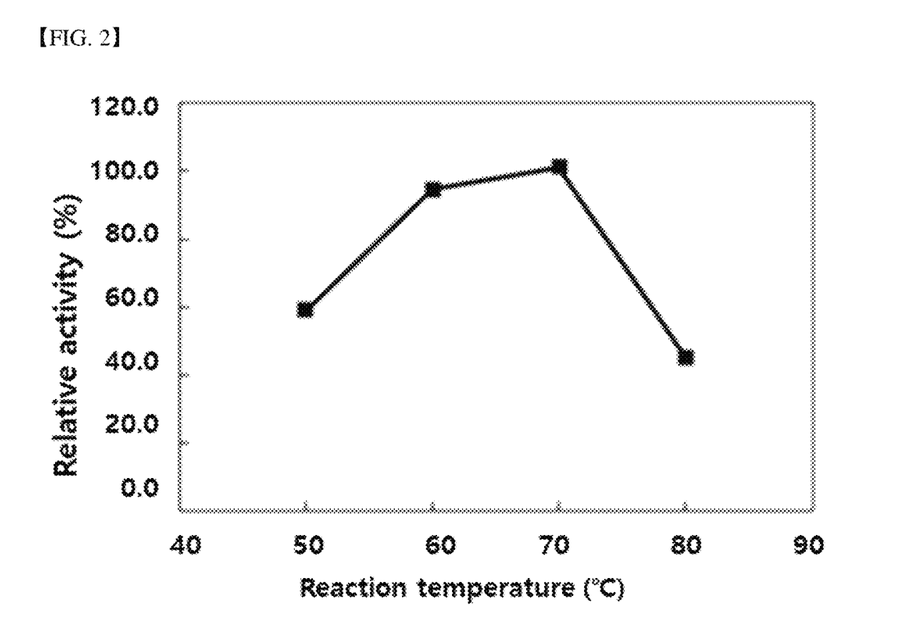
FIG. 2 is a graph showing relative activities of producing psicose of *Microbacterium oxydans* strain isolated in one example of the present invention according to the temperature.
Figure 3:
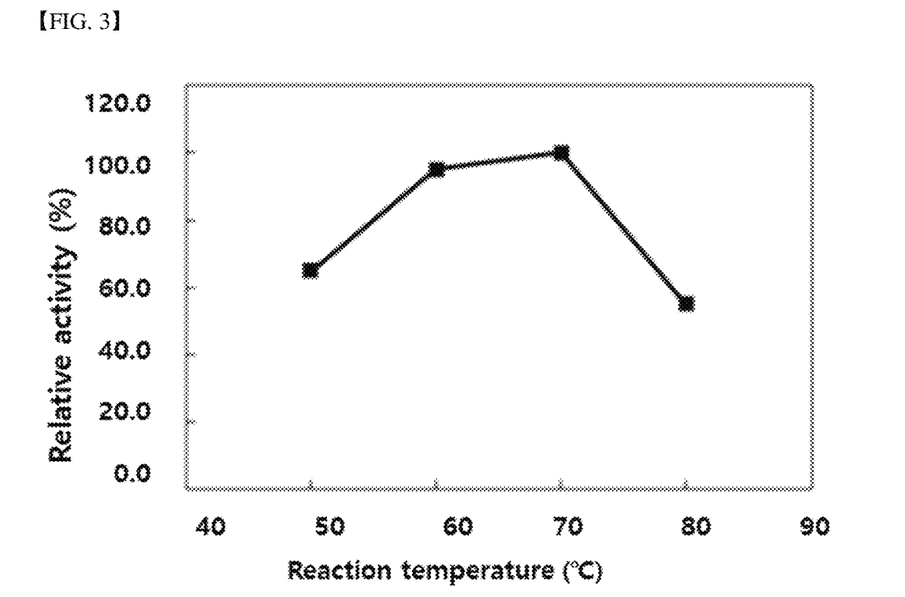
FIG. 3 is a graph showing relative activities of producing psicose of *Microbacterium phyllosphaerae* strain isolated in one example of the present invention according to the temperature.

To confirmed the optimum temperature for producing a psicose, two strains isolated in Example 1 in the concentration of microbial cells of 5 mg(dcw)/mL was reacted in 400 g/L fructose and 1 mM manganese metal ion-added 50 mM PIPES buffer solution (pH 7.0) for 1 hour as changing the temperature in the range of 55 to 80° C., and after the reaction was finished, the production of psicose was measured through HPLC analysis with the same method as Example 1, and the obtained results were shown in FIG. 2 (*M.oxydans* SYG-A1). FIG. 3 (*M.phyllosphaerae* SYG-A2) and the following Table.

TABLE 1

| Reaction temperature (° C.) | *M. oxydans* SYG-A1 Relative activity (%) | *M. phyllosphaerae* SYGA2 Relative activity (%) |
| --- | --- | --- |
| 50 | 59 | 65 |
| 60 | 95 | 95 |
| 70 | 100 | 100 |
| 80 | 45 | 55 |

Figure 1:
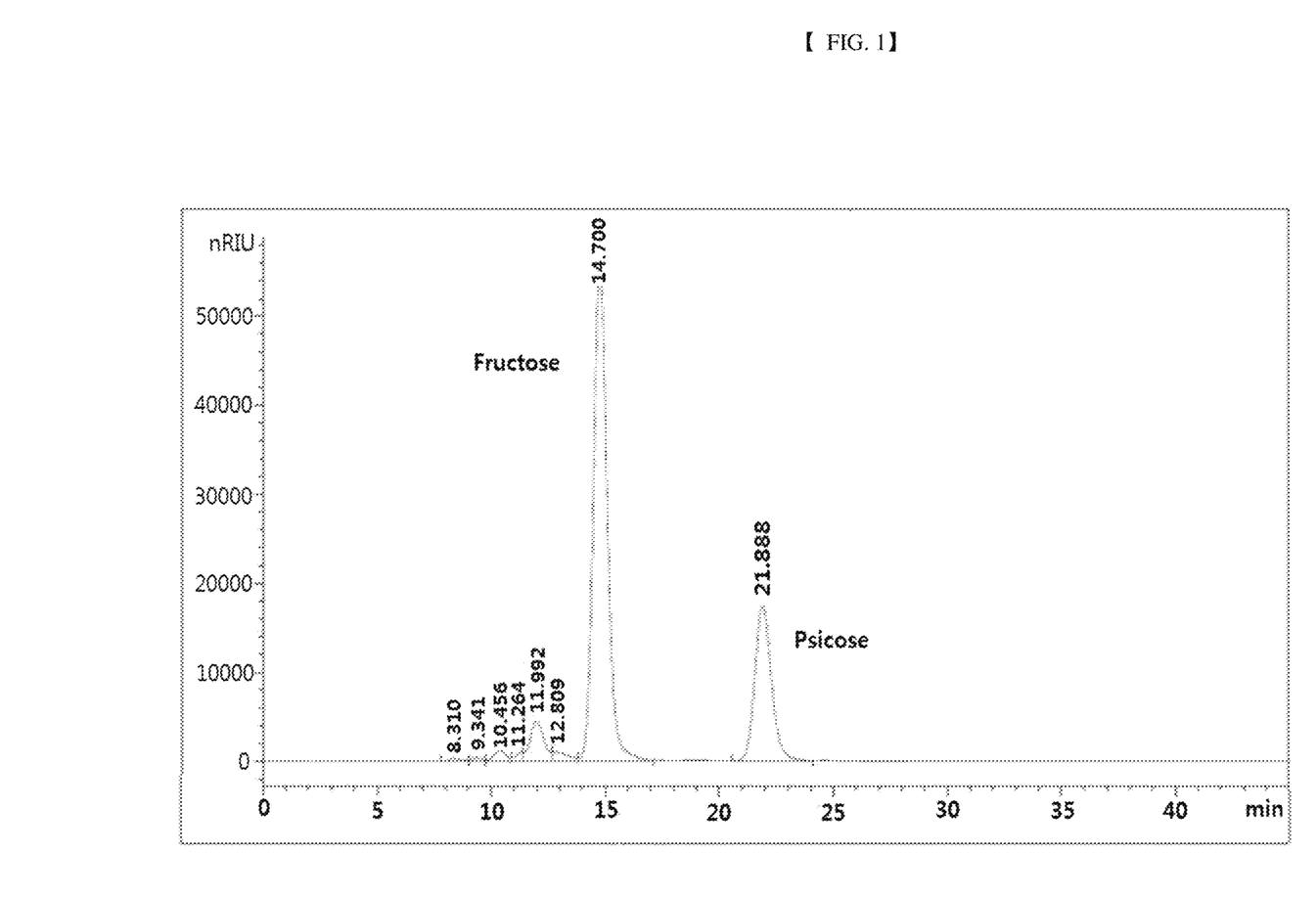
FIG. 1 is a graph showing a chromatogram confirming the psicose produced from the high concentration of fructose by High-Performance Liquid Chromatography (HPLC) in one example of the present invention.

As shown in FIG. 1, FIG. 2 and Table 1, it was confirmed that the relative activity of *M.oxydans* SYG-A1 and *M.phyllosphaerae* SYGA2 was increased as increasing the reaction temperature by 70° C. and decreased at 80° C. In addition, the isolated strains exhibited the maximum activity at the temperature of 70° C.

Example 4. Test for Psicose Productivity

The maximum psicose productivity according to the reaction time was tested. The activities over the reaction time were measured under the conditions of 20 mg/mL of the concentration of microbial cells of strains isolated in Example 1, 400 g/L of the fructose concentration, the temperature of 70° C. and pH 7.0. The reaction was performed for 12 hours and the psicose productivity was confirmed by HPLC analysis in the 2 hour interval. The result was shown in FIG. 4, FIG. 5 and following Table.

TABLE 2

| Reaction Time (hr) | *M. oxydans* SYG-A1 Relative activity (%) | *M. phyllosphaerae* SYG-A2 Relative activity (%) |
| --- | --- | --- |
| 1 | 5.9 | 6 |
| 3 | 6.5 | 8 |
| 5 | 7.5 | 10.5 |
| 7 | 8.8 | 15 |
| 18 | 10.3 | 18.8 |

Figure 4:
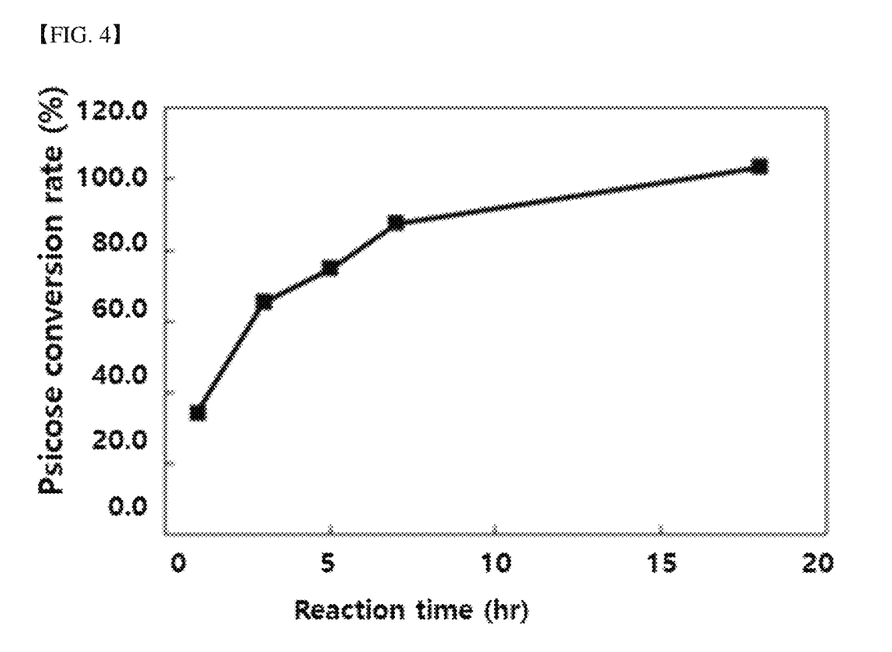
FIG. 4 is a graph showing relative activities of producing psicose of *Microbacterium oxydans* strain isolated in one example of the present invention according to reaction time.
Figure 5:
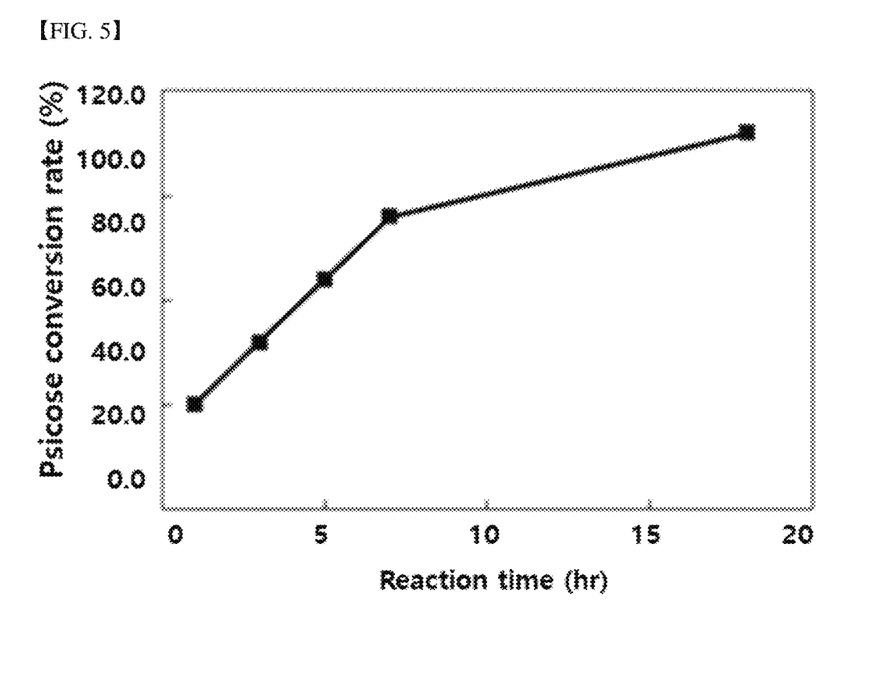
FIG. 5 is a graph showing relative activities of producing psicose of *Microbacterium phyllosphaerae* strain isolated in one example of the present invention according to reaction time.

As shown in Table 2 and FIG. 4, *M.oxydans* SYG-A1 showed the psicose conversion rate increased as the reaction time passed, and in particular, showed the maximum psicose conversion rate as approximately 10.3%, after the reaction at 70° C. for 18 hours, in which the produced psicose was approximately 28 g/L. In addition, as shown in Table 2 and FIG. 5, *M.phyllosphaerae* SYG-A2 showed the psicose conversion rate increased as the reaction time passed, and in particular, showed the maximum psicose conversion rate as approximately 18.8%, after the reaction at 70° C. for 18 hours, in which the produced psicose was approximately 52 g/L.

The invention claimed is:

1. A method for producing a psicose from a fructose-containing substrate using a bacterium belonging to the genus *Microbacterium* having a psicose conversion activity, comprising
reacting the fructose-containing substrate with at least one selected from the group consisting of a microbial cell of the bacterium, a culture of the bacterium, and a lysate of the bacterium in the presence of at least one metal ion selected from the group consisting of manganese ion and cobalt ion,
wherein the bacterium belonging to the genus *Microbacterium* is *Microbacterium phyllosphaerae*,
wherein the *Microbacterium phyllosphaerae* is a strain deposited as an accession number KCCM12034P.

2. The method for producing a psicose of claim 1, wherein the step of reacting is performed by contacting the fructose-containing substrate with a support immobilized with at least one selected from the group consisting of a microbial cell of the bacterium, a culture of the bacterium, and a lysate of the bacterium.

3. The method for producing a psicose of claim 1, wherein the fructose-containing substrate contains fructose at a concentration of 40 to 75% (w/w).

4. The method for producing a psicose of claim 1, wherein the method is characterized by not using a buffer solution.

5. The method for producing a psicose of claim 1, wherein the method is performed under the temperature condition of 40 to 80° C.

6. The method for producing a psicose of claim 1, wherein the method is performed for 1 to 48 hours.

* * * * *